US010646191B2

(12) United States Patent
Wang et al.

(10) Patent No.: US 10,646,191 B2
(45) Date of Patent: May 12, 2020

(54) COLLISION AVOIDANCE SYSTEM AND COLLISION AVOIDANCE METHOD FOR DETECTION BED

(71) Applicant: GENERAL ELECTRIC COMPANY, Schenectady, NY (US)

(72) Inventors: Chunyu Wang, Beijing (CN); Yuqing Li, Beijing (CN); Qiang Zhang, Beijing (CN); Dan Chuang, Beijing (CN)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 626 days.

(21) Appl. No.: 15/105,503

(22) PCT Filed: Dec. 16, 2013

(86) PCT No.: PCT/CN2013/089508
§ 371 (c)(1),
(2) Date: Jun. 16, 2016

(87) PCT Pub. No.: WO2015/089699
PCT Pub. Date: Jun. 25, 2015

(65) Prior Publication Data
US 2016/0361039 A1    Dec. 15, 2016

(51) Int. Cl.
*A61B 6/02* (2006.01)
*A61B 6/00* (2006.01)
(Continued)

(52) U.S. Cl.
CPC ............ *A61B 6/547* (2013.01); *A61B 6/0407* (2013.01); *A61B 6/102* (2013.01); *A61B 6/54* (2013.01)

(58) Field of Classification Search
CPC ...................................................... A61B 6/02
(Continued)

(56) References Cited

U.S. PATENT DOCUMENTS 3,980,288 A * 9/1976 Mitchell ................ A61G 13/02
5/601
5,056,365 A    10/1991 Gray et al.
(Continued)

FOREIGN PATENT DOCUMENTS

CN    200984237    12/2007
CN    201005699    1/2008
(Continued)

OTHER PUBLICATIONS

English translation of the International Search Report for PCT/CN2013/089508, dated Sep. 3, 2014, 2 pages.
(Continued)

*Primary Examiner* — Fredrick C Conley
(74) *Attorney, Agent, or Firm* — Fletcher Yoder, P.C.

(57) ABSTRACT

A collision avoidance system and collision avoidance method for a detection bed are described. The collision avoidance system comprises stress sensors for measuring a stress caused by supporting a bed face of the detection bed and outputting stress data; a collector, which is connected with the stress sensors and is configured to collect the stress data output by each of the stress sensors; a judging processor, which is connected with the collector and is configured to judge whether the collected stress data monotonically changes within a preset time; and a controller connected with the judging processor, the controller controlling the bed face of the detection bed so that it stops moving when the judging processor determines that the collected stress data monotonically changes within the preset time.

10 Claims, 4 Drawing Sheets

(51) Int. Cl.
*A61B 6/04* (2006.01)
*A61B 6/10* (2006.01)

(58) Field of Classification Search
USPC .............................................. 5/601
See application file for complete search history.

(56) References Cited

U.S. PATENT DOCUMENTS

| | | |
|---|---|---|
| 7,857,512 B2 | 12/2010 | Camus |
| 2005/0281374 A1* | 12/2005 | Cheng .................. A61N 5/1049 378/68 |
| 2010/0287703 A1* | 11/2010 | Zapata ................. A61B 6/0457 5/601 |
| 2012/0219099 A1* | 8/2012 | Loukianov ............ H04J 3/0697 375/357 |

FOREIGN PATENT DOCUMENTS

| | | |
|---|---|---|
| CN | 102743180 A | 10/2012 |
| JP | 6437951 | 2/1989 |

OTHER PUBLICATIONS

English translation of the Written Opinion for PCT/CN2013/089508, dated Sep. 3, 2014, 5 pages.

\* cited by examiner

COLLISION AVOIDANCE SYSTEM AND COLLISION AVOIDANCE METHOD FOR DETECTION BED

CROSS-REFERENCE TO RELATED APPLICATIONS

This application is a National Stage Filing under 35 U.S.C. 371 of International (PCT) Application No. PCT/CN2013/089508, filed Dec. 16, 2013, which is incorporated by reference herein in its entirety.

FIELD

The present disclosure relates to a collision avoidance system and method, particularly to a collision avoidance system and method for a detection bed that may be used in a medical application.

BACKGROUND

Medical detection devices such as X-ray, computed tomography (CT), magnetic resonance (MR) and the like have been widely used to monitor diseases. As an important component, a detection bed carries an object to be detected. However, during lifting and lowering of the detection bed, it is possible that a bed face collides with a chair, a stretcher and the like, and sometimes even collides with a patient, thus there exists a larger risk.

In order to solve the above problem, the prior art has put forward a technical solution of triggering an action of stopping lifting and lowering using a switch, in which micro switches are mounted on a plurality of positions at a bottom of the bed face, and when collision takes place at the bed face, the collision force makes one or more of the micro switches suffer a reduced bed face pressure and thereby be triggered to a release state. When the micro switch is released, it issues an alarm signal to external controlling means that may just avoid occurrence of danger by controlling the detection bed to stop movement.

However, since the collision force released by triggering the micro switch will change as a load born by the bed face changes, a judgment on whether a collision has occurred is still not precise enough. For example, in comparison with a zero load, when the bed face carries a heavier patient, the required triggering force will obviously be much larger. In other words, if the bed face collides with the same object at the same rate, a switch may be released without a patient, while it is possible that no switch is released in the case that the bed face carries a heavier patient, and the detection bed cannot stop movement timely at this moment, there existing a larger risk.

SUMMARY

There is a need to provide a collision avoidance system and collision avoidance method for a detection bed, which can control the detection bed to stop moving timely when collision takes place at a bed face of the detection bed, avoiding occurrence of danger.

The non-limiting exemplary embodiments described herein provide a collision avoidance system for a detection bed. The system comprises stress sensors, collector and controller. The stress sensors are configured to measure a stress caused by supporting a bed face of the detection bed and outputting stress data. The collector is connected with the stress sensors and is configured to collect the stress data output by each of the stress sensors; the judging processor is connected with the collector and is configured to judge whether the collected stress data monotonically changes within a preset time; the controller is connected with the judging processor, the controller controlling the bed face of the detection bed to stop moving when the judging processor determines that the collected stress data monotonically changes within the preset time.

The non-limiting exemplary embodiments described herein also provide a collision avoidance method for a detection bed. The method comprises:
measuring a stress caused by supporting a bed face of the detection bed and outputting stress data;
collecting the stress data;
judging whether the collected stress data monotonically changes within a preset time;
controlling the bed face of the detection bed to stop moving if the collected stress data monotonically changes within the preset time.

Other features and aspects will be apparent through the following detailed description, figures and claims.

BRIEF DESCRIPTION OF THE DRAWINGS

The present disclosure can be understood better in light of the description of non-limiting exemplary embodiments with reference to the accompanying drawings, in which.

DETAILED DESCRIPTION

Hereafter, a detailed description will be given for exemplary non-limiting embodiments of the present disclosure. It should be pointed out that in the detailed description of the embodiments, for simplicity and conciseness, it is impossible for the Description to describe all the features of the practical embodiments in details. It should be understood that in the process of a practical implementation of any embodiment, just as in the process of an engineering project or a designing project, in order to achieve a specific goal of the developer and in order to satisfy some system-related or business-related constraints, a variety of decisions will usually be made, which will also be varied from one embodiment to another. In addition, it can also be understood that although the effort made in such developing process may be complex and time-consuming, some variations such as design, manufacture and production on the basis of the technical contents disclosed in the disclosure are just customary technical means in the art for those of ordinary skilled in the art associated with the contents disclosed in the present disclosure, which should not be regarded as insufficient disclosure of the present disclosure.

Unless defined otherwise, all the technical or scientific terms used in the Claims and the Description should have the same meanings as commonly understood by one of ordinary skilled in the art to which the present disclosure belongs. The terms "first", "second" and the like in the Description and the Claims of the present utility model do not mean any sequential order, number or importance, but are only used for distinguishing different components. The terms "a", "an" and the like do not denote a limitation of quantity, but denote the existence of at least one. The terms "comprises", "comprising", "includes", "including" and the like mean that the element or object in front of the "comprises", "comprising", "includes" and "including" covers the elements or objects and their equivalents illustrated following the "comprises", "comprising", "includes" and "including", but do not exclude other elements or objects. The term "coupled" or "connected" or the like is not limited to being connected physically or mechanically, nor limited to being connected directly or indirectly.

Figure 1:
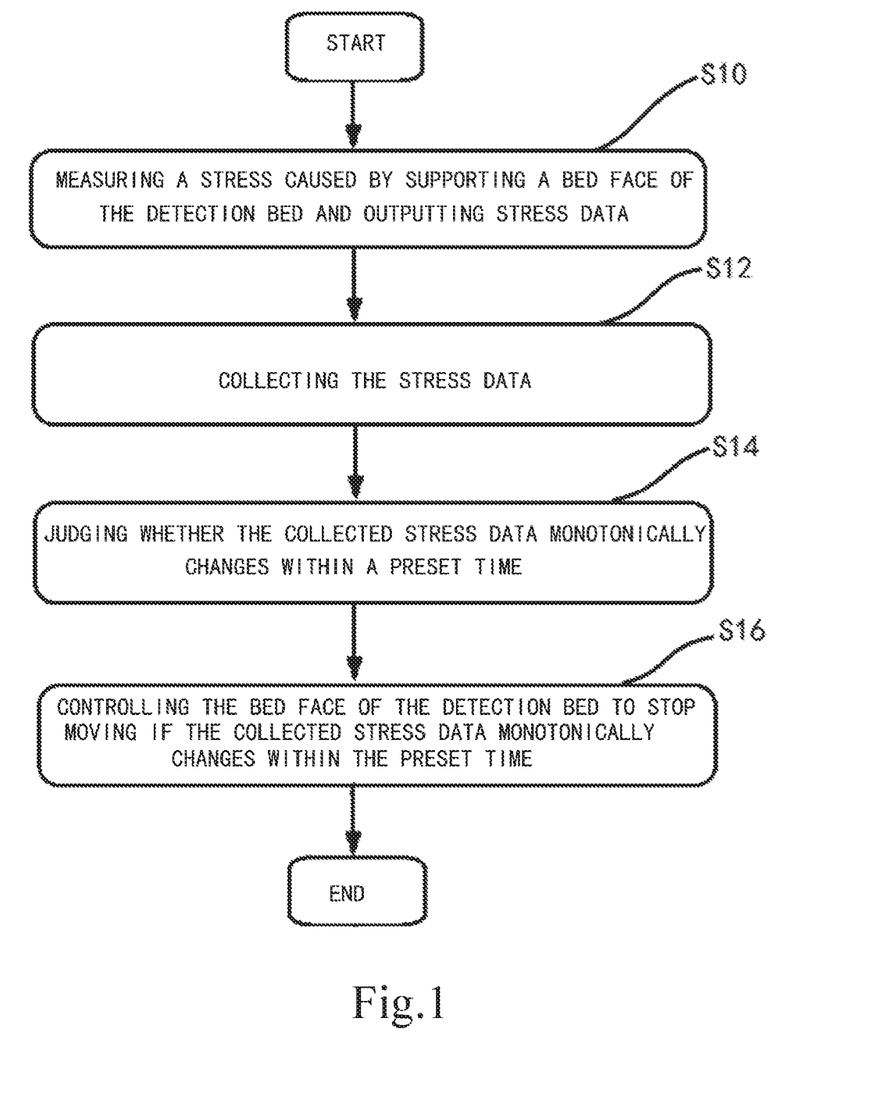
FIG. 1 is a flow schematic chart of an exemplary non-limiting embodiment of a collision avoidance method for a detection bed.
Figure 2:
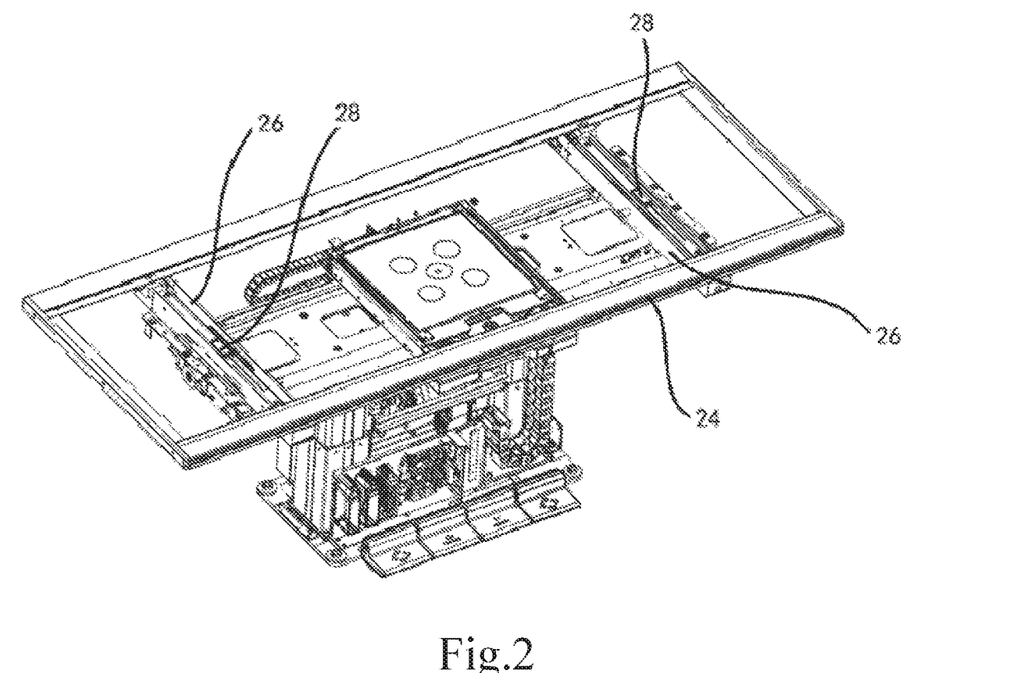
FIG. 2 is a structural schematic diagram of an exemplary non-limiting embodiment in which stress sensors are mounted on a support of the detection bed.

FIG. 1 is a flow schematic diagram corresponding to at least one non-limiting exemplary embodiment of a collision avoidance method for a detection bed. FIG. 2 is a structural schematic diagram corresponding to at least one non-limiting exemplary embodiment in which stress sensors are mounted on a support of the detection bed. The collision avoidance method for a detection bed of the present embodiment can specifically be applied in a detection bed as shown in FIG. 2.

As shown in FIG. 2, the detection bed comprises a bed face of the detection bed and a support 24 that is configured to support the bed face (not indicated) of the detection bed, in which the support 24 includes at least two cross beams 26. The cross beams 26 are arranged along a direction substantially perpendicular to a direction in which the support 24 extends, which are provided underneath the bed face of the detection bed, each of the cross beams 26 being provided with a stress sensor 28. The support 24 and its cross beams 26 are forced from supporting the bed face of the detection bed and the object to be detected (e.g., the patient) carried thereon, thus may have an internal deformation to generate stress. Each of the stress sensors 28 may be configured to measure the stress and output the stress data. When the bed face of the detection bed suffers an external force, e.g., collision takes place during lifting and lowering, there will be a deformation inside the two cross beams to produce a stress change, then the stress data output by the stress sensor 28 at the corresponding position will be changed as well.

By analyzing the change of the stress data, the collision avoidance method for a detection bed of the present embodiment may judge that such change is caused by the collision or is only caused by actions of the patient on the bed face of the detection bed such as lying on his/her side, thus may precisely judge whether collision is just taking place at the bed face of the detection bed.

As shown in FIG. 1, the collision avoidance method for a detection bed of the present embodiment comprises the following Steps S10, S12, S14 and S16.

Step S10: measuring a stress caused by supporting a bed face of the detection bed and outputting stress data.

Step S12: collecting the stress data.

Step S14: judging whether the collected stress data monotonically changes within a preset time.

Step S16: controlling the bed face of the detection bed to stop moving if the collected stress data monotonically changes within the preset time.

In Step S10, for example, since the support 24 and its cross beams 26 both generate stress from supporting the bed face of the detection bed and the object to be detected thereon, condition of force on the bed face of the detection bed can just be analyzed by arranging the stress sensors 28 on the support 24 to measure the stress generated by the support 24 and outputting the corresponding stress data.

Optionally, the above "stress caused by supporting a bed face of the detection bed" is just the stress measured by the stress sensors 28, which specifically includes the stress generated by the support 24.

Furthermore, the above "stress caused by supporting a bed face of the detection bed" includes the stress generated by each of the cross beams 26. Since each of the cross beams 26 is arranged underneath the bed face of the detection bed directly to be connected with the bed face of the detection bed directly, the stress data output by the stress sensors 28 provided on the cross beams 26 reflects a more precise condition of force on the bed face of the detection bed compared with other positions of the support 24.

Step S12 may specifically collect the stress data output by the stress sensors 28 in a preset frequency by collector connected with each of the stress sensors 28.

In Step S14, it is judged whether the collected stress data monotonically changes within a preset time, and it is judged that collision is taking place at the bed face of the detection bed if it does, and otherwise, it is judged that no collision has happened. The above "monotonically change" means that the stress data increases progressively within the preset time, or the stress data decreases progressively within the preset time. The "preset time" may be determined by ways of multiple experiments, for example, occurrence of collision usually leads to a monotonous change of the stress data within a period of time, but the stress change caused by the patient's lying one his/her side within the period of time is usually non-monotonous (e.g., sometimes increase and sometimes decrease), then the period of time may be determined as a "preset time". In the present embodiment, the "preset time" is less than 1 second.

Since collision of the bed face can cause an instantaneous change of the stress, which makes the stress caused by the patient's actions such as lying on one's side, sitting and the like change, and the stress change caused by the collision of the bed face has a larger range within a preset time, i.e., with a larger rate of change, in order to further improve the accuracy for judging collision, in Step S14, "judging whether the collected stress data monotonically changes within a preset time" further comprises: judging whether a rate at which the collected stress data monotonically changes within the preset time reaches a preset value, and if the rate reaches the preset value, it may be judged that collision is taking place at the bed face of the detection bed, and Step S16, i.e., controlling the bed face of the detection bed to stop moving, may be performed, otherwise, it may be judged that no collision has happened, and the bed face of the detection bed may continue to move, e.g., to lift and lower. For example, during lifting and lowering of the bed face of the detection bed, when Step S14 determines that collision is taking place thereon, Step S16 may immediately send a signal to a lifting equipment of the detection bed by controller, to control the lifting equipment to stop moving the bed face of the detection bed, avoiding occurrence of danger.

Figure 3:
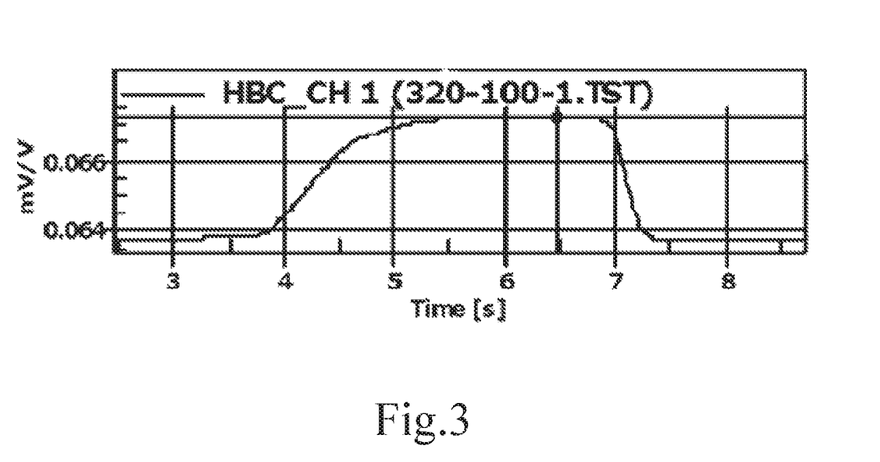
FIG. 3 is a graph of stress data collected from the stress sensors when collision takes place at a bed face of the detection bed according to an exemplary non-limiting embodiment.
Figure 4:
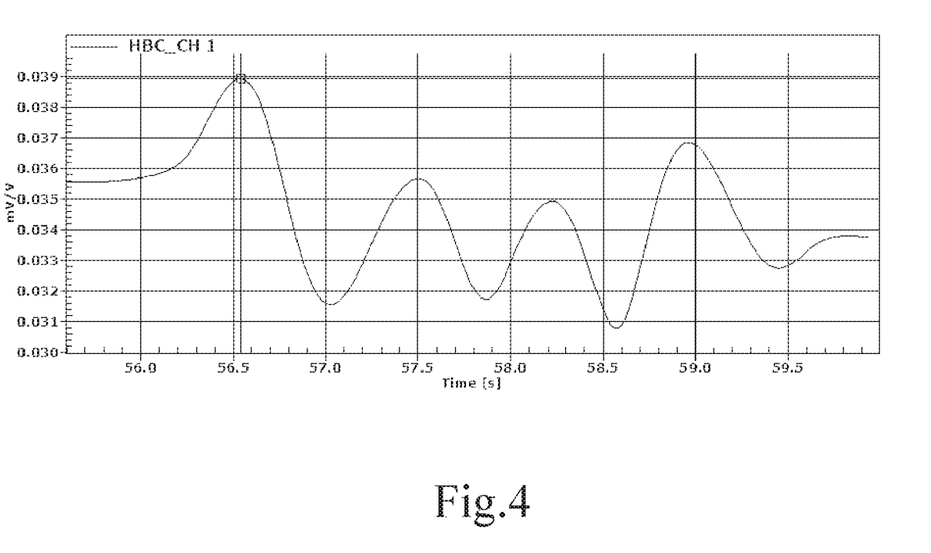
FIG. 4 is a graph of stress data collected from the stress sensors when a patient on the bed face of the detection bed lies on his/her side according to an exemplary non-limiting embodiment.

FIG. 3 is a graph of stress data collected from the stress sensors when collision takes place at a bed face of the detection bed according to at least one non-limiting exemplary embodiment; FIG. 4 is a graph of stress data collected from the stress sensors when a patient on the bed face of the detection bed lies on his/her side according to at least one non-limiting exemplary embodiment. In FIG. 3, within a period of 1 second (such as the period of 4-5 second and the period of 6-7 second as shown in FIG. 3), the stress data monotonically rises or monotonically falls, without a repeated rise or fall, which shows that collision is taking place on the bed face within said period of time, Step S14 shall be performed at this moment to timely control the bed face to stop moving, e.g., stop lifting and lowering; in FIG. 4, within a period of 1 second (such as the period of 56.5-57.5 second as shown in FIG. 4), the stress data first falls then rises, which shows that the stress change is not caused by collision, and lifting and lowering operations may be continued to be performed on the bed face.

Optionally, the stress data output in Step S10 is an analog voltage signal, then the following step is further comprised between Step S10 and Step S12: converting the stress data output in Step S10 from an analog voltage signal into a digital signal.

Moreover, after testing, it can be seen that for different magnitudes of load, the stress generated from supporting the bed face of the detection bed by the support 24 is also different. Then the stress data output by the stress sensors 28 on the same position will be different depending on different magnitudes of load of the bed face, thus the weight of the patient may also be estimated by comparing the following two types of data: the stress data output by the stress sensors 28 when the bed face of the detection bed has a zero load, and the stress data output by the stress sensors 28 when the bed face of the detection bed carries the patient.

Therefore, after Step S10, the collision avoidance method for a detection bed of the present embodiment may further comprise the following step: estimating a weight of an object to be detected by comparing stress data output by the stress sensors 28 when the bed face of the detection bed has a zero load with stress data output by the stress sensors 28 when the bed face of the detection bed carries the object to be detected. By said step, it may be helpful for a doctor to obtain a patient's weight and thus select appropriate parameters for examination according to the patient's weight.

Figure 5:
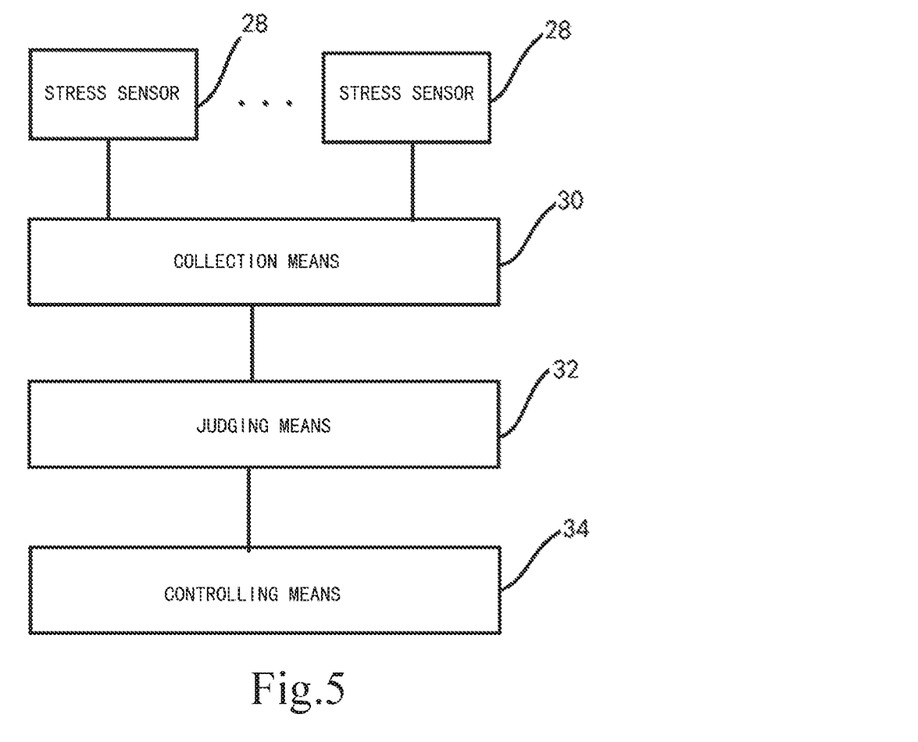
FIG. 5 is a frame schematic diagram of a collision avoidance system for a detection bed provided by an exemplary non-limiting embodiment.

FIG. 5 is a frame schematic diagram of a collision avoidance system for a detection bed provided by at least one non-limiting exemplary embodiment o, in which the collision avoidance system for a detection bed of the present embodiment may specifically be applied to the detection bed as shown in FIG. 2 and may be configured to carry out the collision avoidance method for a detection bed as shown in FIG. 1, which comprises at least one stress sensor 28, collector 30, judging processor 32 and controller 34.

Each of the stress sensors 28 is configured to measure a stress caused by supporting a bed face of the bed and outputting stress data.

The collector 30 is in communication with the stress sensors 28 and is configured to collect the stress data output by each of the stress sensors 28.

The judging processor 32 is in communication with the collector 30, and is configured to determine whether the collected stress data monotonically changes within a preset time and thus judging whether collision is taking place on the bed face of the detection bed. If the collected stress data monotonically changes within the preset time, it shows that collision is taking place on the bed face of the detection bed. The controller 34 is connected with the judging processor 32, and controls the bed face of the detection bed to stop moving when the judging processor 32 determines that the collected stress data monotonically changes within the preset time.

Optionally, the judging processor 32 is further configured to determine whether a rate at which the collected stress data monotonically changes within the preset time reaches a preset value, and the controller 34 is configured to control the bed face of the detection bed to stop moving if the rate reaches the preset value.

Optionally, the above "preset time" is less than 1 second.

In the present embodiment, the collector 30, the judging processor 32 and the controller 34 may be arranged outside the detection bed and integrated together, in which communication with each of the stress sensors 28 is carried out by the collector 30 and signals for controlling are sent to the lifting equipment of the detection bed by the controller 34.

For example, during lifting and lowering of the bed face of the detection bed in FIG. 2, when the judging processor 32 determines that collision is taking place thereon, the controller 34 immediately sends a signal to the lifting equipment of the detection bed to control the lifting equipment to stop moving the bed face of the detection bed, avoiding occurrence of danger.

Furthermore, the above stress sensors may be at least two stress sensors, correspondingly provided on the at least two cross beams of the support, and the at least two cross beams are provided underneath the bed face of the detection bed. For example, as shown in FIG. 2, two stress sensors 28 are provided on the support 24 for supporting the bed face of the detection bed, specifically correspondingly provided on the two cross beams 26 of the support 24.

Optionally, the stress data output by each of the stress sensors 28 is an analog voltage signal, and the collision avoidance system for a detection bed of the present embodiment further comprises an analog/digital converter (not shown in the figure) connected with each of the stress sensors 28 and the collector 30, for converting the stress data output by each of the stress sensors 28 from an analog voltage signal into a digital signal and thereafter sending the converted signals to the collector 30.

Optionally, the collision avoidance system for a detection bed of the present embodiment may further comprise weight estimation means (not shown in the figure), which may be connected with the stress sensors 28. The weight estimation means estimates a weight of the object to be detected by comparing the stress data output by the stress sensors 28 when the bed face of the detection bed has a zero load with the stress data output by the stress sensors 28 when the bed face of the detection bed carries the object to be detected. Accordingly, it may be helpful for a doctor to obtain a patient's weight and thus select appropriate parameters for examination according to the patient's weight.

Figure 6:
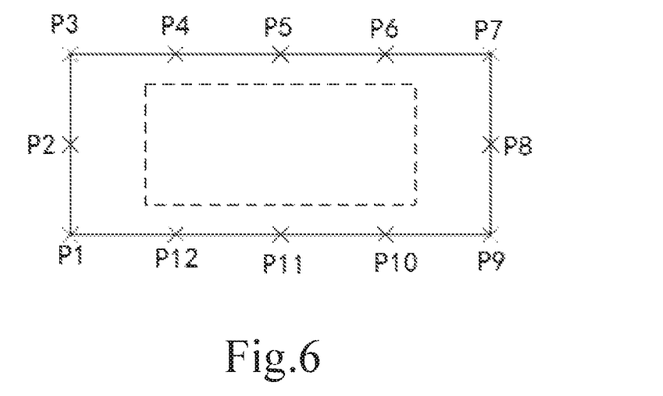
FIG. 6 is a schematic diagram of a detection bed provided by an exemplary non-limiting embodiment showing a plurality of positions where collision takes place.

FIG. 6 is a schematic diagram of a detection bed provided by at least one non-limiting exemplary embodiment, which exemplarily shows a plurality of positions where collision takes place, e.g., P1-P12. Table 1 shows collision force generated on each of the collision positions P1-P12, with the bed face of the detection bed having different magnitudes of load according to at least one non-limiting exemplary embodiment. From Table 1, it can be seen that when the same collision takes place on the same collision position, even if there is a larger difference in the magnitudes of load, the generated collision force will still be substantially the same. Therefore, at the instant moment of collision, the stress change generated by the support will still not have a larger difference due to different magnitudes of load.

TABLE 1

| Collision Position | Collision Force (Kg Force) | | | |
|---|---|---|---|---|
| | Zero Load | 120 Kg Distributed Load | 0 Kg Distributed Load | 320 Kg Distributed Load |
| P1 | 7.5 | 5 | 5 | 10 |
| P2 | 10 | 5 | 7 | 7.5 |
| P3 | 7.5 | 4 | 8 | 8 |
| P4 | 8 | 7 | 7.5 | 8.5 |
| P5 | 8 | 7.5 | 7.5 | 7.5 |
| P6 | 8.5 | 8 | 8.5 | 9 |
| p7 | 8.5 | 9 | 7 | 7.5 |
| p8 | 10 | 7.5 | 8 | 8 |
| p9 | 7.5 | 7.5 | 8.5 | 8.5 |
| p10 | 8 | 7.5 | 7.5 | 8 |
| p11 | 8.5 | 8 | 9 | 7.5 |
| p12 | 9 | 8 | 8 | 8.5 |

Thus, in the collision avoidance system and collision avoidance method for a detection bed provided by the above embodiments, judgment is made by measuring a stress caused by supporting a bed face of the detection bed and collecting stress data. No matter whether the bed face of the detection bed carries a patient or not, collision will always cause an instantaneous change of the stress. Therefore, as long as it is judged that the collected stress data monotonically changes within a preset time, it shows that collision is taking place on the bed face of the detection bed, thus no judgment error due to different loads will be caused. Compared with the prior art, accuracy on judging is greatly improved, such that when collision takes place on the bed face of the detection bed, the bed face can be controlled to stop moving timely, avoiding occurrence of danger.

Some non-limiting exemplary embodiments have been described in the above. However, it should be understood that various modifications may be made thereto. For example, if the described techniques are carried out in different orders, and/or if the components in the described system, architecture, apparatus or circuit are combined in different ways and/or replaced or supplemented by additional components or equivalents thereof, proper results may still be achieved. For example, as a person of ordinary skill in the art will appreciate, one or more of the elements of the collision avoidance system, e.g. the sensors, collector, judging processor and controller, may, individually or in combination, comprise, be linked to or otherwise be in communication with a computer or processor having a memory. Accordingly, other implementations also fall within the spirit and scope of the invention. Hence, the patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A collision avoidance system for a detection bed comprising a bed face, the system comprising:
    stress sensors configured to measure a stress caused by supporting the bed face of the detection bed with and/or without a load on the bed face and outputting corresponding stress data;
    a collector in communication with the stress sensors and is configured to collect the stress data output by each of the stress sensors;
    a judging processor in communication with the collector and configured to determine whether the collected stress data increases progressively or decreases progressively within a preset time period, wherein a progressive increase or progressive decrease in the collected stress data within the preset time period is indicative of the bed face colliding with an object; and
    a controller in communication with the judging processor, the controller configured to control the bed face of the detection bed so that the bed face stops moving when the judging processor determines that the collected stress data increased or decreased progressively within the preset time period.

2. The collision avoidance system of claim 1, wherein the judging processor is further configured to determine whether a rate at which the collected stress data progressively increased or decreased within the preset time period reaches a preset value, and the controller is configured to control the bed face of the detection bed so that the bed face stops moving if the rate reaches the preset value.

3. The collision avoidance system of claim 1, further comprising a support configured to support the bed face of the detection bed, wherein the stress sensors are disposed on the support.

4. The collision avoidance system of claim 3, wherein the support comprises at least two cross beams and the stress sensors comprise at least two stress sensors where at least one stress sensor of the at least two stress sensors is disposed on each of the at least two cross beams.

5. The collision avoidance system of claim 1, further comprising a weight estimator in communication with the stress sensors and configured to estimate a weight of a patient to be detected by comparing stress data output by the stress sensors when the bed face of the detection bed has a zero load with stress data output by the stress sensors when the bed face of the detection bed is loaded with the patient to be detected.

6. A collision avoidance method for a detection bed comprising a bed face, the method, comprising:
    measuring a stress caused by supporting the bed face of the detection bed and outputting corresponding stress data;
    collecting the stress data;
    determining whether the collected stress data increases progressively or decreases progressively within a preset time period, wherein a progressive increase or progressive decrease in the collected stress data within the preset time period is indicative of the bed face colliding with an object; and
    controlling the bed face of the detection bed so that the bed face stops moving if the collected stress data increased or decreased progressively within the preset time period.

7. The collision avoidance method of claim 6, wherein determining whether the collected stress data progressively increased or decreased within the preset time period comprises:
    determining whether a rate at which the collected stress data progressively increased or decreased within the preset time period reaches a preset value, and controlling the bed face so that the bed face stops moving if the rate reaches the preset value.

8. The collision avoidance method of claim 6, wherein the stress caused by supporting the bed face of the detection bed comprises a stress generated by supporting a support of the bed face of the detection bed.

9. The collision avoidance method of claim 8, wherein the support comprises at least two cross beams provided underneath the bed face of the detection bed, the stress caused by supporting the bed face of the detection bed comprising stresses generated by the cross beams.

10. The collision avoidance method of claim 6, wherein after the step of measuring the stress caused by supporting the bed face of the detection bed and outputting corresponding stress data, the method further comprises estimating a weight of a patient to be detected by comparing stress data output by the stress sensors when the bed face of the detection bed has a zero load with stress data output by the stress sensors when the bed face of the detection bed is loaded with the patient to be detected.

* * * * *